United States Patent [19]

Norvell

[11] Patent Number: 5,480,455
[45] Date of Patent: Jan. 2, 1996

[54] LINING MATERIAL FOR USE WITH PROSTHETICS AND SIMILAR DEVICES AND METHOD FOR MAKING AND USING SAME

[75] Inventor: Jean Norvell, Newark, Del.

[73] Assignee: W. L. Gore & Associates, Inc., Newark, Del.

[21] Appl. No.: 123,744

[22] Filed: Aug. 25, 1993

[51] Int. Cl.⁶ ........................................... A61F 2/78
[52] U.S. Cl. .................................... 623/36; 602/63; 2/904
[58] Field of Search ................................. 623/33, 36, 901; 2/904; 264/222; 602/63, 900

[56] References Cited

U.S. PATENT DOCUMENTS

| | | |
|---|---|---|
| 3,600,717 | 8/1971 | McKeehan . |
| 3,802,424 | 4/1974 | Newell . |
| 4,194,041 | 3/1980 | Gore et al. . |
| 4,294,240 | 10/1981 | Thill ............................ 602/21 |
| 4,494,536 | 1/1985 | Latenser . |
| 4,516,572 | 5/1985 | Schlein ......................... 602/3 |
| 4,635,626 | 1/1987 | Lerman ................... 623/36 X |
| 5,016,622 | 5/1991 | Norvell . |
| 5,102,711 | 4/1992 | Keller et al. . |

FOREIGN PATENT DOCUMENTS

| | | |
|---|---|---|
| 0397998 | 11/1990 | European Pat. Off. . |
| 0397999 | 11/1990 | European Pat. Off. . |
| 3820098 | 12/1989 | Germany ..................... 623/33 |
| 1355373 | 6/1974 | United Kingdom . |
| 2213380 | 8/1989 | United Kingdom . |
| 9310732 | 6/1993 | WIPO . |

OTHER PUBLICATIONS

ASTM D751–89; Standard Test Methods for Coated Fabrics.
ASTM D882–91; Standard Test Methods for Tensile Properties of Thin Plastic Sheeting.
Literature: "Comfort Zone;" Silopos, Niagara Falls, N.Y.; Date: Unknown.
Literature: TEC Interface Systems; Comfort; Date: Unknown.
Literature: ICECAST™, ICEROSS™; Cascase Orthopedic Supply, Inc.; Date: Unknown.
Brochure: 35 Shuttle Lock; Brandywine Prosthetic, New Castle, Del.; Date: Unknown.

Primary Examiner—David H. Willse
Attorney, Agent, or Firm—David J. Johns

[57] ABSTRACT

An improved liner and method is taught for use in protecting a wearer's skin from moisture retention when worn with prosthetic devices and other substantially non-breathable shells. The liner is form fitted to attach to a wearer without bunching or other pressure points which can cause skin irritation. Preferably, the liner comprises a membrane of expanded polytetrafluoroethylene coated on its interior surface with a polyurethane material to aid in moisture isolation and to protect the liner from compromise due to oils and other contaminants found in perspiration. The liner is effective at shielding a wearer's skin from moisture even when worn with no separate absorbent layer.

9 Claims, 4 Drawing Sheets

LINING MATERIAL FOR USE WITH PROSTHETICS AND SIMILAR DEVICES AND METHOD FOR MAKING AND USING SAME

BACKGROUND OF THE INVENTION

1. Field of the Invention

The present invention relates to liners for use with prosthetics and similar devices worn in close contact with a wearer's skin where dissipation of perspiration is a concern.

2. Description of Related Art

A common problem in placing any material with low or no air permeability ("breathability") in contact with a wearer's skin is that perspiration cannot evaporate and tends to build-up between the skin and the non-breathable material. With only passing use, this condition leads to an uncomfortable damp or clammy feeling. In more extreme circumstances, such as with the prolonged use of a prosthetic device covering a limb, the accumulation of moisture fully hydrates the skin, which in its softened, wet condition leads to skin irritation, maceration, and rapid bacteria growth.

The problem of moisture build-up with prosthetic use is a particularly serious one. Generally prosthetic devices such as artificial limbs must be constructed from durable material to withstands the vigors of use. Materials such as metal or high impact plastic provide the necessary degree of durability, but offer very poor breathability.

The problem of moisture build-up in the interface with prosthetic devices is particularly dangerous for diabetic patients, and especially those experiencing Peripheral Vascular Disease (PVD). PVD is a major cause of amputation in the United States and a patient typically experiences amputation of a lower limb within 20 years of its onset. This is because impaired circulation affects nerve endings, so sensation is decreased, and minor bruising, rubbing or skin irritation can occur without the patient experiencing any discomfort. A minor break in the skin can quickly lead to ulceration, possible gangrene and eventual amputation.

Dry skin normally equates to healthy skin and this is particularly true for certain high risk groups, such as a diabetic with PVD. Use of a non-breathing attachment to a prosthetic device, such as neoprene or silicone, which is fitted as a second skin having little or no air gap, necessitates frequent changes of a separate absorbent layer, or else moisture vapor generated by the pores of the wearer's skin transforms to liquid and hydrates and softens the skin. When totally hydrated, "immersion skin" develops and any pressure or movement caused by loose fitting prosthesis or liner on the softened skin results in a blister type formation, and large areas of skin debraiding.

To address the problem of moisture build-up, traditionally the wearer of a prosthetic device has employed a thick sock of wool or similar material between his or her skin and the prosthetic. This has accomplished a number of important functions, including providing a wick to remove perspiration from the skin, improving the fit between the wearer and the device, and cushioning the wearer from shock during usage. Unfortunately, the sock performed none of these functions particularly well. As a wick, a conventional sock device tends to be good at initial moisture removal, but will eventually become saturated with moisture requiring repeated changing. Additionally, with materials such as wool, odor control with the wet material was another unpleasant problem. Due to constraints of conventional materials, the sock-type device was even poorer in performance in providing fit and comfort to the wearer. As a result, conventional prosthetics did not fit well and offered meager shock absorption.

More recent advances have provided vast improvements in the fit and shock absorption of prosthetic devices. The inclusion of tight fitting interfaces of neoprene or silicone rubber and similar materials assure that devices can be kept snugly in place during use and that the wearer will be effectively cushioned from shock. Regrettably, these materials only worsen the problem of moisture retention, with the tighter elastomeric fit offering reduced opportunity for moisture dissipation and the typical cushioning layer being poor at removing moisture away from the wearer's skin.

In response to some of these concerns, it was proposed in UK Patent Application GB 2,213,380, published Aug. 16, 1989, to form a limb cover from a waterproof yet breathable microporous expanded polytetrafluoroethylene (PTFE) membrane which will permit the passage of moisture through it into an absorbent layer such as a sock. The absorbent sock serves to absorb perspiration and allows it to evaporate from the exposed surfaces of the sock; the membrane serves to prevent perspiration from passing back through to the wearer's skin. In order to get the membrane to fit on the wearer's limb, it is taught that a single membrane should be cold formed into a cup-shaped area suitable for insertion of the limb. The excess remainder of the membrane is then folded and wrapped around the sides of the limb.

While the above device may work well for its intended purposes, it simply fails to address many of the concerns presented by improved prosthetic devices. First, the method of forming and wearing the PTFE membrane is simply inadequate for comfortable use of improved cushioning devices. For example, when inserted into a tight fitting silicone sleeve regularly worn between the wearer and the prosthesis, the bunching of the PTFE material around the side of the limb can lead to chafing and masceration.

Second, the use of non-absorbent devices like silicone sleeves o simply cannot provide the absorbance sought with absorbent wool or acrylic socks. As a result, either the silicone sleeve must be worn over the absorbent sock—diminishing fit and feel, or the material must be worn without an absorbent layer—removing the intended mechanism for dissipating the moisture.

Third, the British reference does not address the concern that expanded PTFE membranes can become contaminated with oils from the body which can result in loss of their water repellency. This may be of limited concern when worn in contact with an absorbent layer which can wick moisture away from the membrane, but is fatal to the operation of the device if the membrane is employed with no absorbent layer.

A different use of a lining material is disclosed in U.S. Pat. No. 5,016,622 issued May 21, 1991, to Jean Norvell. This device comprises a tube or wrap of expanded PTFE used as a liner for orthopedic casts. The tube or wrap is covered with a layer of padding (e.g. cotton or polyester), from which evaporation can occur, which is in turn coated with the immobilizing layer of the cast. Although this device works quite well for its intended purposes, the teaching of this patent again relies upon a separate absorbent layer to dissipate moisture away from the wearer as well as a rigid casting material, cushioned by padding, open at the distal and proximal ends of the cast. This construction guarantees a small air gap will remain between the skin and the casting material to allow the evaporation of moisture.

By contrast, a prosthetic device is custom fitted to a wearer as a "second skin" through a process of negative and positive molds. As such, the prosthesis represents the exact contours of the wearer's limb, with virtually no ease allowed whatsoever. In fact, in some prostheses, a partial vacuum is deliberately induced within the interface to the limb to ensure increased fit in the device and the total exclusion of any air gap. In this respect U.S. Pat. No. 5,016,622 offers no instruction of how to improve the interface between a prosthetic device and its wearer.

In other fields besides prosthetics, similar concerns have arisen. For example, it is common practice in many sports such as football and ice hockey to employ extensive pads and braces to protect against injury. The more extensive of these pads generally comprise hard, impervious shells with a layer of foam or other resilient material coated within. Not surprisingly, in the course of athletic contests a tremendous moisture build-up can occur within these pads which can lead to discomfort and skin irritation. While various absorbent materials such as cotton or polymer fabrics are regularly worn under some of these pads to absorb excess moisture, this provides only limited relief and does not serve to isolate the wearer's skin adequately from the perils of moisture build-up.

Other areas of concern where moisture-build up can occur beneath a non-breathable material include the use of orthotic body supports, cam walkers and other orthotics, orthosis systems, and braces, as well as immobilizing braces and devices used to treat cumulative trauma disorders. Additionally, moisture accumulation is likewise a problem with other pads and safety garments (e.g. flak jackets) which provide limited breathability while worn in intimate contact with the skin.

Accordingly, it is a primary purpose of the present invention to provide a liner for a substantially non-breathable shell worn against a wearer's skin which effectively isolates moisture from the wearer skin.

It is another purpose of the present invention to provide such a liner which provides a smooth fit between the wearer and the shell so as to avoid problems of chafing and other skin irritation.

It is still another purpose of the present invention to provide such a liner which can be safely worn in direct contact with a wearer's skin, even during periods of excess perspiration, without compromising its effectiveness.

It is an additional purpose of the present invention to provide a liner which can effectively isolate a wearer's skin from moisture even when worn without a separate absorbent layer.

It is yet another purpose of the present invention to provide methods for constructing and employing such a liner which will provide the above benefits.

These and other purposes of the present invention will become evident from review of the following specification.

SUMMARY OF THE INVENTION

The present invention is an improved liner for use with prosthetics, orthotics, and similar substantially non-breathable devices, and method for construction and use, to protect a wearer's skin from moisture retention.

The liner of the present invention is form-fitted over the wearer's body and preferably comprises a membrane of a water repellent yet moisture vapor permeable material, such as expanded polytetrafluoroethylene (PTFE), which has been coated on its interior surface with a layer of hydrophilic/oleophobic material, such as polyurethane. The interior coating serves to protect the PTFE membrane from compromise due to oils found in perspiration and is further believed to contribute to the moisture isolating properties of the present invention.

The liner may be constructed in the following manner. First, two layers of the membrane are formed, each in the outline of that part of the wearer's body over which the non-breathable device is to be worn. The membrane layers are then heat sealed together to form a flat, smooth seam along all but one open end of the liner. When a limb is inserted into the open end of the liner, the liner will form a smooth fit over the limb, with no bunching or raised pressure points which might tend to cause skin irritation.

In use, the liner of the present invention is extremely effective at isolating a wearer's skin from moisture hydration over an extended period of time, even without the presence of a separate absorbent layer. As such, the liner of the present invention can be worn in intimate contact between a wearer's skin and a substantially non-breathable shell without compromising the fit and feel interface between the wearer and the shell.

DESCRIPTION OF THE DRAWINGS

The operation of the present invention should become apparent from the following description when considered in conjunction with the accompanying drawings, in which.

DETAILED DESCRIPTION OF THE INVENTION

The present invention is an improved liner for use in a variety of applications where prosthesis or other relatively impermeable shell is worn in intimate contact with a wearer's skin.

Figure 1:
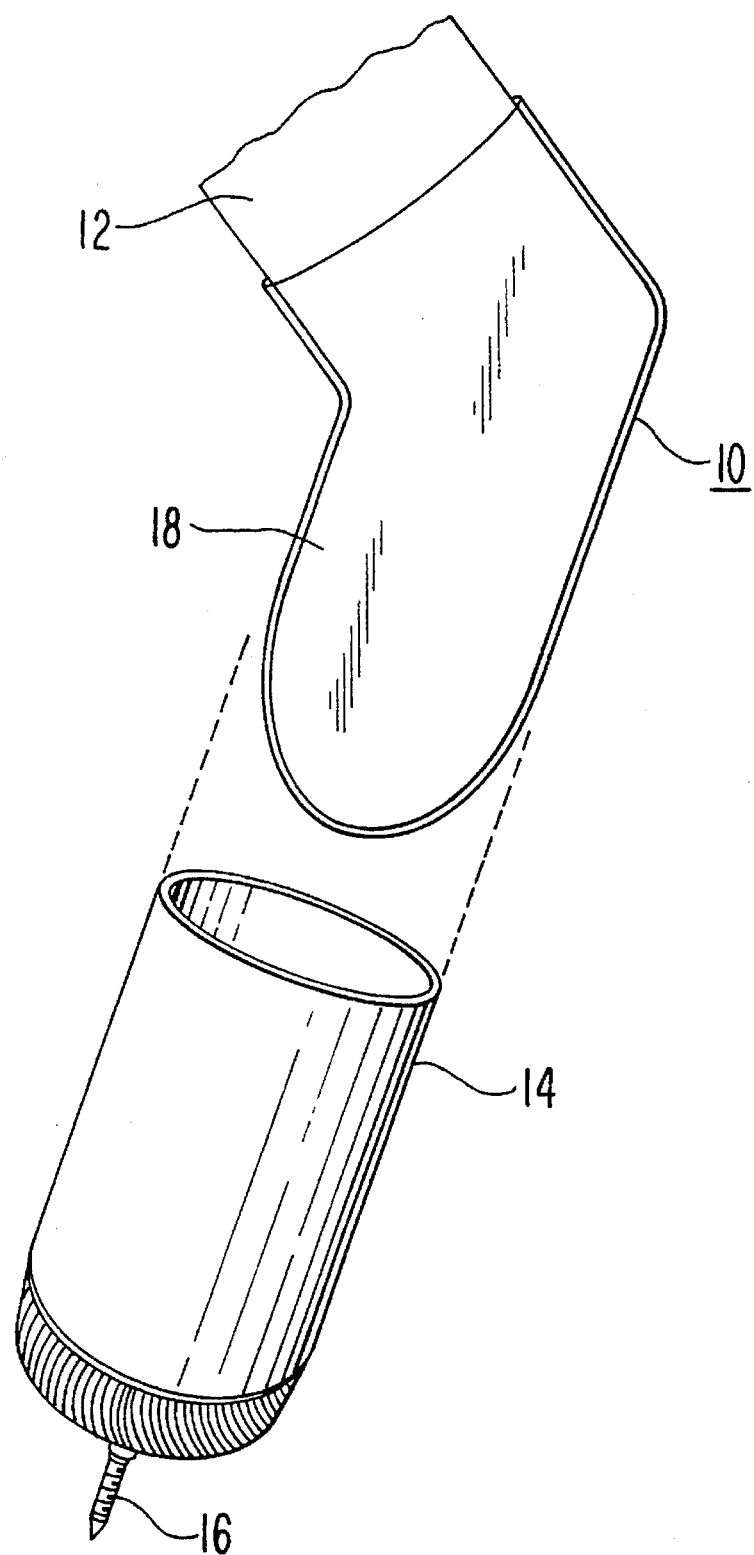
FIG. 1 is an elevational view of a liner of the present invention shown worn on a wearer's limb and shown in exploded orientation with a silicone sleeve to which a prosthetic device is attached.

Shown in FIG. 1 is a liner 10 of the present invention shown worn over a limb 12 of an amputee. As is commonly employed today, a tight fitting elastic silicone sleeve 14 is worn over the limb 12 to provide a mechanism for attachment of a prosthetic device, such as through the use of a bolt or screw device 16 adapted to be attached to a complementary device in the prosthetic. In addition to providing a secure interface with the prosthetic, the elastic sleeve 14 also serves to cushion the wearer's limb 12 during use. Unfortunately, most materials used as a sleeve which provide the necessary degree of fit and cushion also tend to be impermeable to moisture vapor transmission, thus making moisture build-up within the sleeve a distinct dilemma.

In order to address this problem, the liner 10 of the present invention is constructed from a membrane 18 that is water repellent yet moisture vapor permeable. In this way, perspiration from the wearer's skin can dissipate through the membrane in a vapor form, but cannot re-penetrate the membrane as a condensate.

Preferably, the membrane 18 employed in the present invention comprises a sheet of polytetrafluoroethylene (PTFE) which has been expanded to create a network of fibrils interconnecting polymeric nodes. This material is resistant to water penetration while permitting the transmission of moisture vapor through it. Such a product can be produced in a known manner, such as in accordance with the teachings of U.S. Pat. No. 3,953,566 issued Apr. 27, 1976, to Gore.

One concern with this material is that its waterproof properties can be compromised by contamination with certain oils, such as those excreted by the body in perspiration. This problem can be corrected by treating one side of the expanded PTFE membrane with a continuous coating of a hydrophilic/oleophobic material such as polyurethane which permits the passage of moisture vapor but shields the expanded PTFE material from oil contamination. One such laminate is disclosed in U.S. Pat. No. 4,194,041 issued Mar. 18, 1980, to Gore et al. Other polyurethanes which may be useful for this purpose are described in U.S. Pat. Nos. 4,532,316 issued Jul. 30, 1985, to Henn, and 4,942,214 issued Jul. 17, 1990, to Sakhpara.

Suitable coated expanded membrane materials which can be employed in the present invention are manufactured in a variety of forms by W. L. Gore & Associates, Inc., of Elkton, Md., under the trademark GORE-TEX®. The preferred material comprises a composite expanded PTFE film coated with a continuous hydrophilic/oleophobic polyurethane layer and weighing approximately 29 $g/m^2$. This material is identified by W. L. Gore & Associates, Inc. under specification Part Number 20048-1, Level 3, ISO 9000.

By way of example, one suitable membrane tested as suitable for use in the present invention comprises a composite with the follow characteristics: (1) a microporous expanded PTFE membrane having a mass of about 17 $g/m^2$; approximately a 80% pore volume; a resistance to air flow (Gurley Number) of approximately 5 seconds; and a Bubble Point of approximately 20 psi; and (2) a continuous, nonporous coating of polyurethane applied to the microporous expanded PTFE membrane in accordance with U.S. Pat. No. 4,194,041 in a layer comprising approximately 12 $g/m^2$. The presently preferred polyurethane comprises a HYPOL 2000 hydrophilic pre-polymer available from W. R. Grace & Co., Lexington, Mass., cured with an amine curing agent.

The composite membrane has the following properties: a Burst Strength (restrained) of 170 psi; a Moisture Vapor Transmission Rate (MVTR) of approximately 13,000 $g/m^2$/day; a tensile strength of about 4,000 psi in the transverse direction and about 2,400 psi in the longitudinal direction; and a weight of about 29 $g/m^2$.

The resistance of the uncoated membrane to air flow was measured by a Gurley densometer (in accordance with ASTM Standard D726-58) manufactured by W. & L. E. Gurley & Sons. The results are reported in terms of Gurley Number which is the time in seconds for 100 cubic centimeters of air to pass through 1 square inch of a test sample at a pressure drop of 4.88 inches of water.

The Bubble Point of porous PTFE was measured using isopropyl alcohol following ASTM Standard F316-86. The Bubble Point is the pressure of air required to blow the first continuous bubbles detectable by the their rise through a layer of isopropyl alcohol covering the PTFE media. This measurement provides an estimation of maximum pore size.

Burst Strength was measured by employing a modified procedure similar to that set forth in ASTM Standard D751-89 employing a Mullen Type Hydrostatic Tester. The ASTM procedure was followed, except that a support of 1.8 oz. nylon taffeta fabric was applied over the membrane composite to prevent it from excessively stretching and breaking prematurely. The indicated pressure was the pressure at which water pressure ruptured the restrained membrane composite.

The Moisture Vapor Transmission Rate (MVTR) was determined by mixing approximately 70 ml of a solution consisting of 35 parts by weight of potassium acetate and 15 parts by weight of distilled water and placing it into a 133 ml polypropylene cup, having an inside diameter of 6.5 cm at its mouth. An expanded polytetrafluoroethylene (PTFE) membrane having a minimum MVTR of approximately 85,000 $g/m^2$/24 hrs. as tested by the method described in U.S. Pat. 4,862,730 to Crosby and available from W. L. Gore & Associates, Inc. of Newark, Del., was heat sealed to the lip of the cup to create a taut, leakproof, microporous barrier containing the solution. A similar expanded PTFE membrane was mounted to the surface of a water bath. The water bath assembly was controlled at 23° C. plus 0.2° C., utilizing a temperature controlled room and a water circulating bath.

The sample to be tested was allowed to condition at a temperature of 23° C. and a relative humidity of 50% prior to performing the test procedure. Samples were placed so the microporous polymeric membrane was in contact with the expanded polytetrafluoroethylene membrane mounted to the surface of the water bath and allowed to equilibrate for at least 15 minutes prior to the introduction of the cup assembly.

The cup assembly was weighed to the nearest 1/1000 g and was placed in an inverted manner onto the center of the test sample. Water transport was provided by the driving force between the water in the water bath and the saturated salt solution providing water flux by diffusion in that direction. The sample was tested for 5 minutes and the cup assembly was then removed, weighed again within 1/1000 g. The MVTR of the sample was calculated from the weight gain of the cup assembly and was expressed in grams of water per square meter of sample surface area per 24 hours.

The tensile strength was determined in accordance with ASTM D-882 (Tensile Properties of Thin Plastic Sheeting) using an Instron Tensile Tester, Series IX.

The above described material addresses the concern that the membrane 18 must be maintained waterproof even under conditions with heavy sweat contamination. As such, the inclusion of a continuous polyurethane or similar oleophobic coating on the expanded PTFE membrane serves to protect the waterproof properties of the membrane even when the membrane is exposed to extensive perspiration.

For reasons not fully understood to date, far better performance of the present invention has been observed when the polyurethane coated side of the membrane is oriented in direct contact with the wearer's skin. When worn in this manner, the skin remains dry, even when the wearer is generating excessive perspiration (e.g. by lifting weights or other strenuous activities) while wearing a prosthetic device without an absorption or evaporation media on the other side of the membrane.

It is a further important property of the liner 10 of the present invention that it is adapted to fit precisely over the wearer's limb 12 to create a smooth and sometimes snug or tight interface between the wearer and the prosthetic sleeve 14. Due to the close fit provided by the sleeve, there is very little tolerance for any bunching or pressure points of the liner 10 within the sleeve 14. Accordingly, the liner 10 should be sized to match the contours of that portion of the wearer's body over which it is applied. One method of producing a fitted liner 10 is shown in FIGS. 2 and 3.

Figure 2:
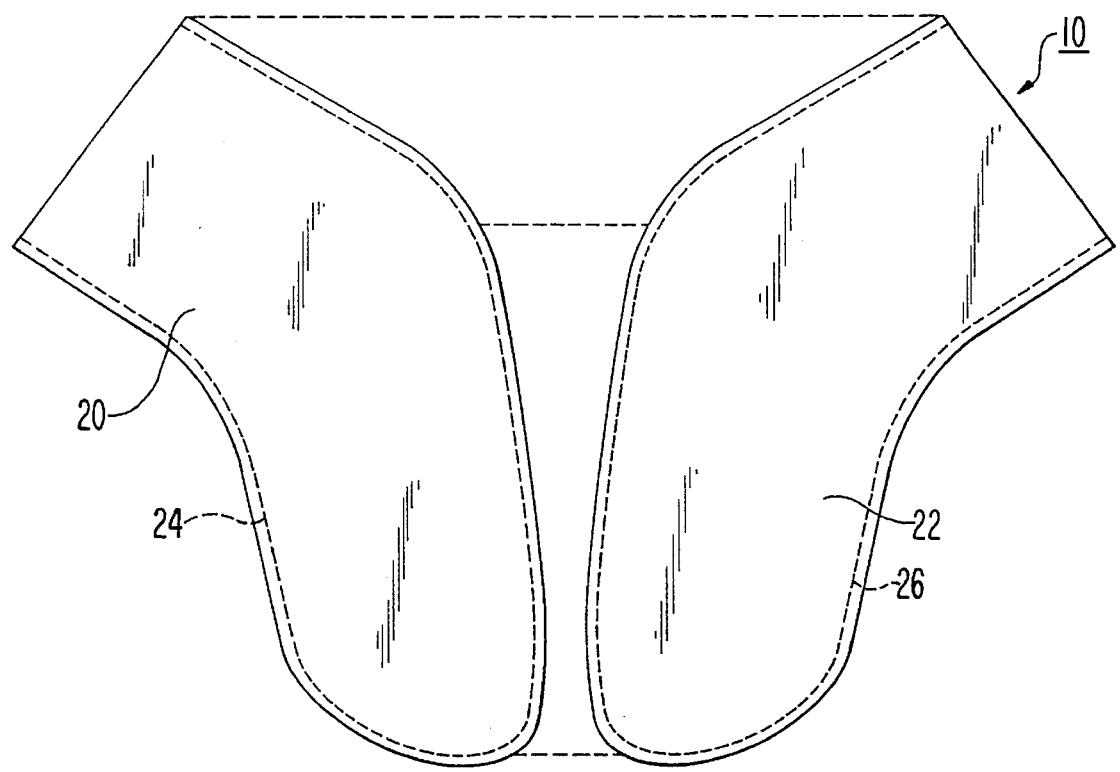
FIG. 2 is a side view of two halves of a membrane used to form a liner of the present invention.
Figure 3:
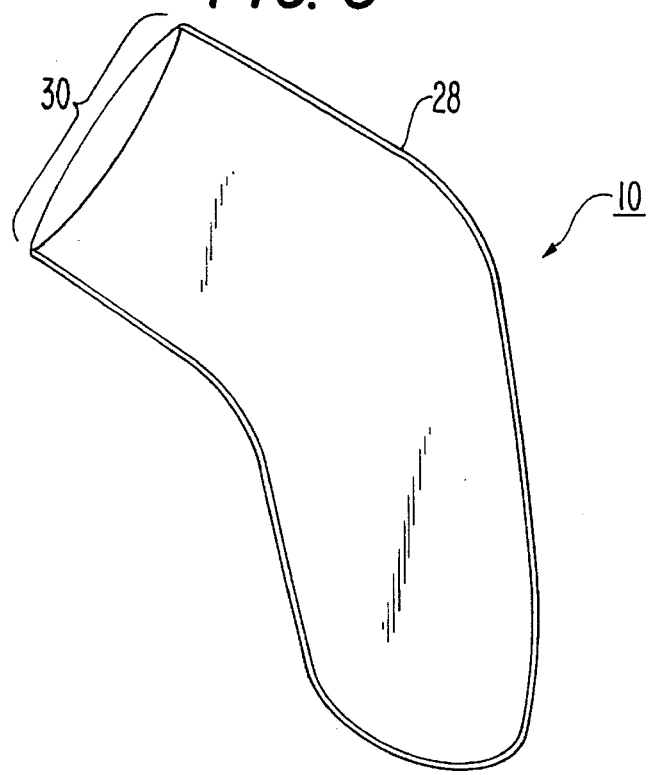
FIG. 3 is a side view of the liner of the present invention assembled from the membrane segments shown in FIG. 2.

As is illustrated in FIG. 2, the membrane 18 is cut into two segments 20, 22, each segment matching the outline of the part of the wearer's body over which the membrane is to be worn. Additional material should be provided around the edge of the membrane segments as shown.

Figure 4:
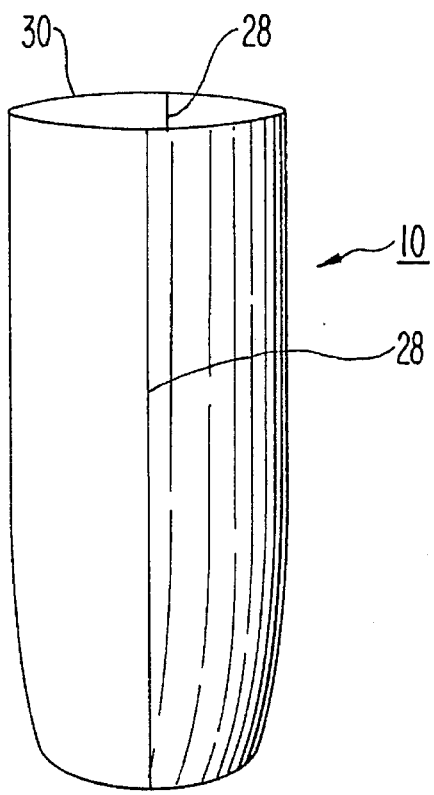
FIG. 4 is a front view of the liner shown in FIG. 3.

Once the segments 20, 22 are prepared, the two segments are mounted over top of one another to form two layers of matching shape. The polyurethane coated sides of each segment of the membrane should be positioned inwardly to abut themselves. Once oriented in this manner, a heated pen or similar device is applied along outline lines 24, 26 to fuse the two layers together. By using a heat source of approximately 200° C. (within a general range of 200° to 350° C.), the polyurethane will serve to bond the membrane segments together as is shown in FIGS. 3 and 4.

The ideal seal comprises an even seam 28 of approximately ⅛ inch extending partially around the edge of the membrane segments along a first portion. A second portion, end 30, of the membrane is left unsealed to allow insertion of the wearer's limb. Once sealed in this manner, any excess material on the outside of the seam 28 can be cut and removed.

When the liner is formed in this manner, the seam 28 comprises a very thin and smooth joint which lies completely flat in use. When the liner is constructed in this manner and placed on the wearer, it will form a snug fit around the wearer's limb and provide a smooth interface between the wearer and the shell. Due to probable densification of the material, the seam 28 actually is of little or no greater height than the surrounding material. As such, the liner 10 can be worn completely flush with the wearer's skin, with no ridge or other bunching of material to cause skin irritation. This condition is particularly important for applications where substantial weight must be applied through the liner 10, such as in use with a leg prosthetic or body orthotic, where any irritating pressure points must be avoided.

Figure 5:
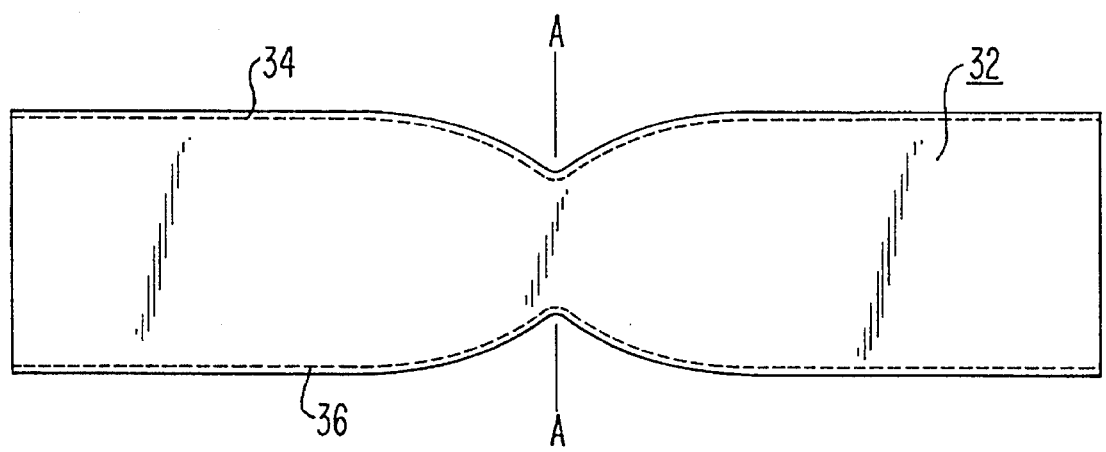
FIG. 5 is a plan view of another embodiment of a liner of the present invention, wherein the liner is constructed from a single segment of membrane.

Another method of constructing the liner of the present invention employs a single sheet of membrane material 32 which is folded upon itself to form both layers of the liner. As is shown in FIG. 5, the membrane 32 comprises a doubly long sheet. The membrane 32 is folded along line A—A and each side is sealed along seam lines 34, 36. A liner formed in accordance with this construction has the additional advantage of no seam line whatsoever at its base, where the greatest pressure points are often experienced.

It should be evident from this description that the liner of the present invention may be constructed from a variety of patterns and in a variety of shapes to address particular applications. For example, while an excessive number of seams is to be avoided both for ease in construction and to reduce the number of possible pressure points, in some instances it may be desirable to construct the liner from three or more pieces of membrane material sealed together to create a smooth, fitted liner.

Figure 6:
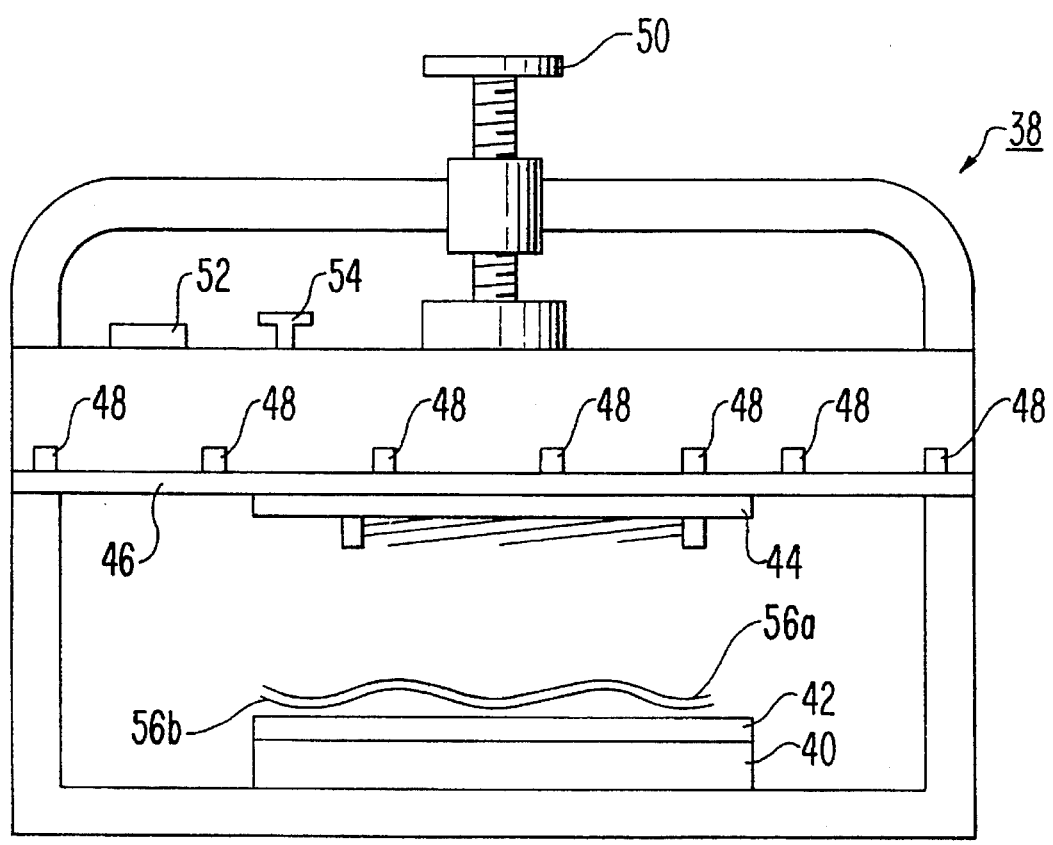
FIG. 6 is a side elevational view of a press apparatus used in the construction of liners of the present invention.

For higher speed construction of identically shaped liners, a heated press 38 can be employed such as that shown in FIG. 6. In this embodiment a four post hydraulic press, such as a DANLY brand press, is paired with a heated platen employing multiple cartridge heaters having a temperature range from room temperature to 450° C. The press 38 comprises: a anvil 40 with a resilient silicone coating 42; a die 44 in the shape of the liner; a heated platen 46, including multiple cartridge heating units 48, in thermally conductive communication with the die 44; a height adjustment mechanism 50; and a temperature indicator 52 and temperature control 54.

In operation, the layers of membrane 56a, 56b are placed upon the coated anvil and positioned beneath the die 44. The die is heated to sealing temperature. For a polyurethane coated expanded PTFE, the sealing temperature is between 200° and 350° C. Once the press 38 has reached the desired temperature, the press is closed to place the die in sealing contact against the membrane 56a, 56b for 1.5 to 3 seconds and then released. Once sealed, the liners can be trimmed of peripheral material. It should be evident that multiple liners can be formed in this manner simultaneously.

Once formed, the liner of the present invention can be worn in direct contact with the wearer's skin. Since the liner is form-fitted to match the contours of that portion of the wearer's body to which a prosthesis is attached, the liner can be worn as a sole layer in direct contact with both the skin and the prosthesis. No intermediate sock or other cushioning layer is required. Additionally, the very thin nature of the membrane employed in the present invention allows its use in even very snug fitting silicone sleeves and similar devices without any discomfort or the need for re-sizing of existing devices.

One of the most notable properties of the present invention is its ability to effectively remove moisture from a wearer's skin without the presence of a separate absorbent layer. Without intending to limit the present invention to such theory, it is believed that the presence of the hydrophilic layer of the membrane in intimate contact with the wearer's skin serves to encourage the removal of moisture while the expanded PTFE membrane prevents condensed moisture from re-penetrating to the skin to cause problems.

In initial tests to date, the use of the membrane alone between an amputee's skin and a silicone sleeve has proven very effective at protecting the skin from moisture build-up and the skin irritation and problems inherent with it. These results are in stark contrast to the use of a conventional absorbent layer where irritation and rash quickly develop.

The present invention is particularly intended for use with prosthetic devices, such as artificial limbs, surface bearing sockets, sleeves, braces, and sheaths. Additionally, the liner of the present invention may have numerous other useful applications, such as orthotic body supports, orthosis systems, and orthotic braces, body jackets, spinal braces, fraction orthotics, cam walkers, etc.

It should be understood from the above list of possible applications, the present invention can be readily employed in any instance where a wearer must don any substantially non-breathable shell.

While particular embodiments of the present invention have been illustrated and described herein, the present invention should not be limited to such illustrations and descriptions. It should be apparent that changes and modifications may be incorporated and embodied as part of the present invention within the scope of the following claims.

The invention claimed is:

1. A process for producing a liner for a substantially non-breathable shell, the liner being worn in tight contact between the shell and a portion of a wearer's body whereby substantial weight is applied through the liner to the shell, which comprises:

providing a thin membrane which is water repellent yet facilitates adequate moisture vapor transmission;

positioning at least two layers of the membrane together;

forming the liner by sealing a first portion of the two layers of membrane together into a shape that complements an outline of the part of the wearer's body which will be in contact with the liner, wherein a flat seam which will not irritate the wearer is created along the seal between the two layers of the membrane;

separating a second portion of the liner to permit the insertion of the part of the wearer's body between the two layers of the membrane and provide a smooth fit of the liner between the shell and the wearer's body whereby the smooth fit protects the wearer from irritating pressure points when substantial weight is applied through the liner; and positioning the liner between the wearer and the substantially impermeable shell so as to cause the liner to separate and maintain excess moisture apart from the wearer's skin.

2. The process of claim 1 which further comprises folding the membrane upon itself to form the two layers of the membrane positioned together.

3. The process of claim 1 which further comprises sealing the first portion of the two layers of membrane together by applying heat to an intended seam between the membranes in excess of the melting temperature of at least a portion of the membrane.

4. The process of claim 3 which further comprises providing as the membrane a sheet of expanded polytetrafluoroethylene (PTFE);

sealing the two layers of PTFE membrane together by applying a heat of at least 200° C.

5. The process of claim 1 which further comprises providing as the membrane a sheet of expanded polytetrafluoroethylene;

treating one side of the membrane to protect against compromise of the water repellent/breathable properties of the membrane by excretions from the wearer; and orienting each such treated side of the membrane inwardly when the two layers of the membrane are attached together.

6. The process of claim 5 which further comprises treating the membrane to protect against compromise of its properties by coating the membrane with a polyurethane.

7. The process of claim 1 which further comprises trimming from the membrane excess material outside of the outline.

8. The process of claim 1 which further comprises applying the liner between the wearer and a shell comprising a sleeve interface with a prosthetic device.

9. The process of claim 8 which further comprises placing the sleeve over the liner and leaving no air gap therebetween.

* * * * *